United States Patent [19]

Bayer et al.

[11] Patent Number: 4,798,299

[45] Date of Patent: Jan. 17, 1989

[54] PIVOT RING

[75] Inventors: Antonius L. Bayer, Rumpt; Bernhardus A. L. Bles, Woerden; Godfrey Hands, Vianen; Dag A. Hovden, Utrecht, all of Netherlands

[73] Assignee: SKF Industrial Trading and Development Co. B.V, Nieuwegein, Netherlands

[21] Appl. No.: 930,699

[22] Filed: Nov. 13, 1986

[30] Foreign Application Priority Data

Dec. 19, 1985 [NL] Netherlands .................. 8503517

[51] Int. Cl.$^4$ .............................................. B66C 23/84
[52] U.S. Cl. .................................. 212/157; 212/253; 384/448
[58] Field of Search ............... 212/149, 150, 153, 155, 212/157, 253; 73/620, 634; 384/513, 548, 448

[56] References Cited

U.S. PATENT DOCUMENTS

| 3,316,037 | 4/1967 | Schaeffler | 384/448 |
| 3,592,052 | 7/1971 | DiGiacomo | 73/620 |
| 3,969,926 | 7/1976 | Walker et al. | 73/620 |
| 4,092,053 | 5/1978 | Riegler et al. | 384/448 |

FOREIGN PATENT DOCUMENTS 1556339  2/1970  Fed. Rep. of Germany .

Primary Examiner—Joseph F. Peters, Jr.
Assistant Examiner—Stephen P. Avila
Attorney, Agent, or Firm—Rosen, Dainow & Jacobs

[57] ABSTRACT

An improved pivot ring assembly which has a first and second annular member, one of which is mounted within the other, the first and second annular members having a first and second spaced apart race, respectively, that face one another, and rolling elements positioned to roll on the races between the first and second annular members. The improvement comprises an aperture being provided in the first annular member for receiving an ultrasonic probe, the aperture having a hole therein which is directed toward a critical area of the assembly. This critical area includes an edge of the race of the second annular member. Furthermore, the races lie in planes perpendicular to the centerline of the annular members, and the first annular member is mounted within the second annular member. Additionally a bevel is formed adjacent to the race of the second annular member, and the axis of said hole extends perpendicular to the bevel and intersects the bevel radially outwardly of the center thereof, whereby an ultrasonic probe mounted in the aperture can scan the area upon relative rotation of the annular members for detecting material defects in said assembly.

9 Claims, 1 Drawing Sheet

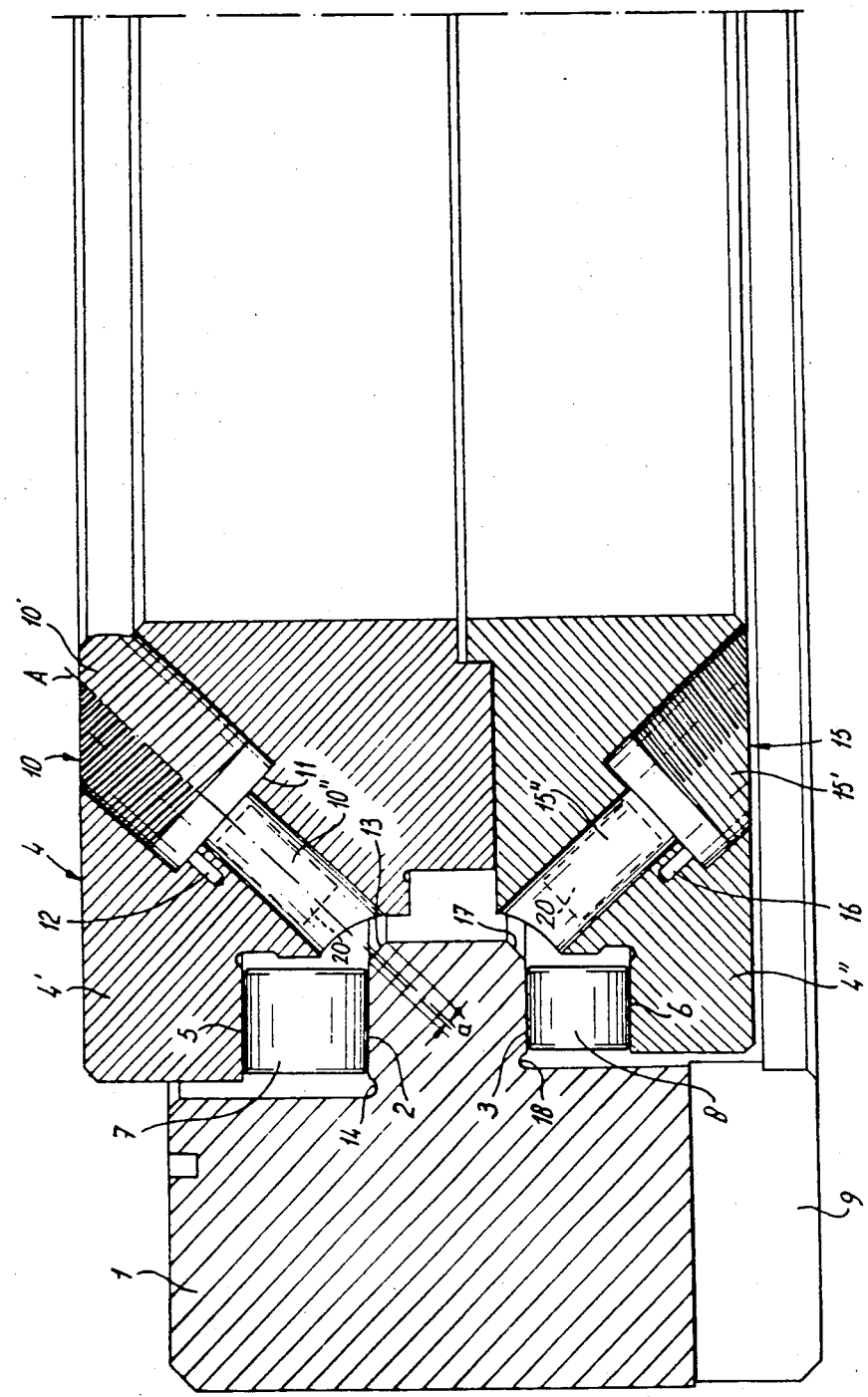

PIVOT RING

The invention relates to a pivot ring comprising two annular members placed one within the other, the outer member being provided on the inside and the inner member on the outside with at least one race so formed that each race of the outer member faces a race of the inner member at a distance to accommodate a circulating series of rolling elements in between them.

Pivot rings are generally known and serve for the rotatable mounting of comparatively heavy pieces of equipment. In particular, pivot rings are used in cranes for mounting the boom assembly to rotate about a vertical axis relative to a substructure, the pivot ring being required to assume great forces and moments of force in alternating directions.

Because the perfect condition of such a pivot ring is of vital importance, and the pivot ring specifically is heavily loaded in operation, there are regulations under which the pivot ring must be frequently inspected for the timely discovery of material defects, especially crack formation in the ring.

Heretofore, it has been necessary for this purpose to dismantle the entire hoist apparatus for proper inspection of the annular members of the pivot ring, and afterwards to reassemble the equipment, which are time-consuming operations during which, moreover, the hoist system is out of service. Furthermore, it has been found that the result of such an inspection would often be that the pivot ring was still in perfect condition, so that the inspection was in a sense unnecessary, whereas on the other hand the inspection may have come too late, in showing that a crack has already begun to form.

The object of the invention is to provide a pivot ring of the type described that can be inspected without need to dismantle the entire system in which the pivot ring is installed.

This object is accomplished in that, according to the invention, it has been realized that by means of at least one ultrasonic probe located in an opening made in one of the annular members of the pivot ring, the critical areas of the pivot ring, which is to say those parts of the pivot ring in which material defects may chiefly manifest themselves in consequence of the loads, can be scanned and possible material defects detected, the said opening being moreover so arranged that it will hardly if at all affect the general strength of the pivot ring.

The opening to accommodate an ultrasonic probe preferably comprises a hole drilled in one of the annular members of the pivot ring, the centerline of the said hole being directed at the innermost edge of a race of the other annular member.

In a pivot ring where the races of the annular members lie in planes perpendicular to the centerline of the pivot ring, preferably the said hole is made in the inner annular member, and the centerline of the hole is directed perpendicular to a bevel on the inner edge of the race of the outer annular member and displaced a slight distance outward from the center of the said bevel.

It is noted that it is known per se, for example from U.S. Pat. No. 3,969,926, that an ultrasonic probe may be used to detect material defects.

The invention will be further explained with reference to the drawing, in which a pivot ring according to the invention is shown in radial section by way of example.

As shown in the drawing, the pivot ring comprises an outer annular member 1 having two races 2 and 3 on the inside of said member, and an inner annular member 4 consisting of two parts 4' and 4', provided with two races 5 and 6 facing the races 2 and 3 respectively of the outer member 1. Between races 2 and 5 a series of rolling elements 7 are located, and between races 3 and 6 a series of rolling elements 8.

In the lower face of the outer annular member 1, a groove 9 extending radially is formed, which serves to mount the member 1 on the substructure of a crane for example.

In part 4' of the inner annular member 4, a hole 10 is arranged, consisting of an internally threaded outer portion 10' and an inner portion 10' of smaller diameter. In the shoulder 11 formed at the transition from the portion 10' of larger diameter to the portion 10' of smaller diameter, a plurality of blind holes 12 are provided. The centerline A of the hole 10 is perpendicular to a bevel 13 on the inner edge of the race 2, this centerline A being displaced outward by a distance a from the center of the bevel 13. In the hole 10, an ultrasonic probe depicted generally by reference numeral 20 of otherwise known type, may be fixed, and means of direction the probe may be set in the blind holes 12, by means of which probe, material defects in the critical areas comprising the bevel 13, the race 2 and the fillet 14 at the inner edge of the race 2 can be scanned and inspected.

In the same manner as the hole 10, a hole 15 is arranged in part 4", comprising an internally threaded portion 15' and a portion 15" of smaller diameter, a set of blind holes 16 being provided as before. In the hole 15, another ultrasonic probe 20 may be fixed, directed at the bevel 17 on the extreme edge of the race 3, by means of which material defects may be detected at the bevel 17 of race 3 and the fillet 18.

We claim:

1. In a pivot ring assembly comprising first and second annular members, one of which is mounted within the other, said first and second annular members having first and second spaced apart races, respectively, that face one another, and rolling elements positioned to roll on said races between said first and second annular members; the improvement wherein an aperture is provided in said first annular member for receiving an ultrasonic probe, said aperture being directed toward a critical area of said assembly, whereby an ultrasonic probe mounted in said aperture can scan said area upon relative rotation of said annular members for detecting subsurface material defects in said assembly.

2. The assembly of claim 1 wherein said aperture comprises a hole in said first member directed toward an edge of the race of said second annular member.

3. The assembly of claim 2 wherein said races lie in planes perpendicular to the centerline of said annular members and said first annular member is mounted within said second annular member, and further comprising a bevel adjacent the race of said second annular member, the axis of said hole extending perpendicular to said bevel.

4. The assembly of claim 3 wherein the axis of said hole intersects said bevel radially outwardly of the center thereof.

5. The assembly of claim 1 wherein said ultrasonic probe is permanently disposed within its aperture provided therefore whereby subsurface material defects can be detected without the requirement of disassembling said pivot ring assembly.

6. In a pivot ring assembly comprising first and second annular members, one of which is mounted within the other, said first and second annular members having first and second spaced apart races, respectively, that face one another, and rolling elements positioned to roll on said races between said first and second annular members; the improvement wherein a hole is provided in said first annular member and an ultrasonic probe is mounted in said hole, said hole being directed toward a critical area of said assembly, whereby said ultrasonic probe mounted in said hole can scan said area upon relative rotation of said annular members for detecting subsurfaces material defects in said assembly.

7. In a pivot ring assembly comprising first and second annular members, said second member having a second race adjacent its radial inner periphery and extending in a plane perpendicular to the axis of said second member, said first member having a first race extending in a plane parallel to the axis of said first member, said first member being mounted with said first race parallel to, facing and axially spaced from said second race, and rolling elements positioned to roll on said races between said first and second annular members; the improvement wherein a hole is provided in said first annular member and an ultrasonic probe is mounted in said hole, said hole being directed toward a portion of said second annular member between said first and second annular members, whereby said ultrasonic probe mounted in said hole can scan said portion upon relative rotation of said annular members for detecting material defects in said assembly without disassembly of said pivot ring assembly.

8. The pivot ring assembly of claim 7 wherein said second annular member has a bevel radially inwardly of said second race, said portion of said second annular member comprising said bevel.

9. In a pivot ring assembly comprising first and second annular members, one of which is mounted within the other, said first and second annular members having first and second spaced apart races, respectively, that face one another, and rolling elements positioned to roll on said races between said first and second annular members; the improvement wherein an aperture is provided in said first annular member for receiving an ultrasonic probe, said aperture comprises a hole which is directed toward a critical area of said assembly said critical area including an edge of the race of said second annular member, and wherein said races lie in planes perpendicular to the centerline of said annular members and said first annular member is mounted within said second annular member, and further comprising a bevel adjacent the race of said second annular member, the axis of said hole extending perpendicular to said bevel and intersects said bevel radially outwardly of the center thereof, whereby an ultrasonic probe mounted in said aperture can scan said area upon relative rotation of said annular members for detecting material defects in said assembly.

* * * * *

UNITED STATES PATENT AND TRADEMARK OFFICE
CERTIFICATE OF CORRECTION

PATENT NO. : 4,798,299

DATED : January 17, 1989

INVENTOR(S) : Bayer et al.

It is certified that error appears in the above-identified patent and that said Letters Patent is hereby corrected as shown below:

Column 2, line 15, change "10'" second occurrence, to --10"--.
Column 2, line 17, change "10'" second occurrence, to --10"--.
Column 2, line 25, change "direction" to --directing--.
Column 3, line 15, change "subsurfaces" to --subsurface--.

Signed and Sealed this

Twenty-ninth Day of October, 1991

*Attest:*

HARRY F. MANBECK, JR.

*Attesting Officer*   *Commissioner of Patents and Trademarks*